(12) United States Patent
Karki et al.

(10) Patent No.: US 11,151,719 B2
(45) Date of Patent: Oct. 19, 2021

(54) AUTOMATIC BRIGHTNESS AND CONTRAST CONTROL NEURAL NETWORK FOR MEDICAL DIAGNOSTIC IMAGING

(71) Applicant: Caide Systems, Inc., Lowell, MA (US)

(72) Inventors: Manohar Karki, Lowell, MA (US); Kye Wook Lee, Groton, MA (US); Jung Hwan Cho, Dracut, MA (US)

(73) Assignee: Caide Systems, Inc., Lowell, MA (US)

( * ) Notice: Subject to any disclaimer, the term of this patent is extended or adjusted under 35 U.S.C. 154(b) by 129 days.

(21) Appl. No.: 16/720,277

(22) Filed: Dec. 19, 2019

(65) Prior Publication Data

US 2020/0202524 A1 Jun. 25, 2020

Related U.S. Application Data

(60) Provisional application No. 62/781,756, filed on Dec. 19, 2018, provisional application No. 62/864,538, filed on Jun. 21, 2019.

(51) Int. Cl.
*G06T 7/00* (2017.01)
*G06T 5/00* (2006.01)
*G06K 9/62* (2006.01)

(52) U.S. Cl.
CPC .......... *G06T 7/0012* (2013.01); *G06K 9/6289* (2013.01); *G06T 5/008* (2013.01); *G06T 2207/10081* (2013.01); *G06T 2207/10088* (2013.01); *G06T 2207/20081* (2013.01); *G06T 2207/20084* (2013.01)

(58) Field of Classification Search
CPC ................... G06T 7/0012; G06T 5/008; G06T 2207/20084; G06T 2207/10088; G06T 2207/20081; G06T 2207/10081; G06T 2207/30016; G06T 5/009; G06T 2207/10072; G06T 2207/10116; G06K 9/6289; G16H 50/20; G16H 30/40; G06N 3/084; G06N 3/0454
See application file for complete search history.

(56) References Cited

U.S. PATENT DOCUMENTS

| | | | |
|---|---|---|---|
| 2010/0249592 A1* | 9/2010 | Langeland | G06T 7/246 600/443 |
| 2013/0290006 A1* | 10/2013 | Kamath | G16H 50/20 705/2 |
| 2020/0160544 A1* | 5/2020 | Yao | G06F 3/0484 |

OTHER PUBLICATIONS

Hyunkwang Lee; Myeongchan Kim; and Synho Do: "Practical Window Setting Optimization for Medical Image Deep Learning"—2018; Machine Learning for Health Workshop at NeurIPS; pp. 1-7. (Year: 2018).*

(Continued)

*Primary Examiner* — Siamak Harandi
(74) *Attorney, Agent, or Firm* — Occhiuti & Rohlicek LLP

(57) ABSTRACT

This invention relates to estimating the window width and window level (center) which are typically used to view and then transform diagnostic imaging data to grayscale images. These grayscale images are then used to check the presence of diseases or abnormalities. For each individual diagnostic image, this invention automatically estimates the most appropriate values. This automatic estimation is done by a specialized module added on to a convolutional neural network-based disease detection system.

11 Claims, 10 Drawing Sheets

(56) References Cited

OTHER PUBLICATIONS

Manohar Karki; Junghwan Cho; Eunmi Lee, Myong-Hun Hahm; Sang-Youl Yoon; Myungsoo Kim; . . . : ("CT Window Trainable Neural Network for Improving Intracranial Hemorrhage Detection by Combining Multiple Settings"; 2020, 2019; Artificial Intelligence in Medicine (106) (Year: 2020).*

Junghwan Cho; Ki-Su Park; Manohar Karki; Eunmi Lee; . . . "Improving Sensitivity on Identification and Delineation of Intracranial Hemorrhage Lesion Using Cascade Deep Learning Models"; Jan. 24, 2019; Society for Imaging Informatics in Medicine 2019; pp. 450-461. (Year: 2019).*

* cited by examiner

AUTOMATIC BRIGHTNESS AND CONTRAST CONTROL NEURAL NETWORK FOR MEDICAL DIAGNOSTIC IMAGING

CROSS REFERENCE TO RELATED APPLICATIONS

This application claims the priority of U.S. Provisional Application No. 62/781,756, filed on Dec. 19, 2018, and U.S. Provisional Application No. 62/864,538, filed on Jun. 21, 2019, the contents of which are hereby incorporated by reference in their entirety.

BACKGROUND

Windowing or adjusting the window-level settings (width and center) in diagnostic images especially Computed Tomography (CT), X-ray and Magnetic Resonance images is quite common to highlight certain regions and lesions. The window width and window level/center values are also referred to as window/level settings. CT images use Hounsfield Units (HU) to represent the radio-densities. The range of the values in the images can be quite big and small difference can often not be easily differentiated. With years of research, different anatomical parts of the body are assigned different window-level settings as default for viewing [1]. Even within the same anatomy, tissues, blood, bones etc. have different default values set so that interesting areas can be easily highlighted. Density difference from normal anatomies can be helpful to identify anomalies and lesions.

Aside from direct clinical use, grayscale images are generated with these default thresholds values and they are further used for research and study. CT images in raw format are processed at a window setting. Generally, the values in these images are in Hounsfield Unit (HU) which can range from −1000 (air) to 30000 (heavy metals) [2]. Different window settings highlight different aspects of the anatomy. The window level (or center) sets the starting point of the HU values and the width represents the range to include. When the width is narrow, objects with a smaller range of densities are visible. This can be useful to isolate a certain anatomy, lesion or other regions of interest. As the window width is increased, even though more regions and anatomies are displayed, they can be harder to distinguish.

However, the default window settings are also not always enough to detect subtle differences from normal images and there have also been various studies where these subtle appearances of malignancy went undetected. For instance, Costelloe et. al. [3] concluded that the use of bone windows provided better specificity when evaluating bone tumors. Similarly, liver window settings have also been used to improve conspicuity of small renal cell carcinomas [4]. There have been several approaches to use different window settings to improve stroke detection from CT images [5]. Stroke window settings is another window setting where the CT images are re-examined but has been criticized for not being appropriate [6]. The approaches where standard window settings are optimized [7] and variable window settings are used in [8] have been introduced to improve acute stroke detection. Both these approaches require manual intervention.

Deep learning technologies have also aided radiological image analysis and contributed to detections of abnormalities in patient data [9] [10] [11]. These abnormalities are not visible at every brightness and contrast settings of the images. Radiologists need to manually go through the diagnostic images carefully and at different settings to detect them. Based on the manual inspection of the grayscale images generated at different thresholds, radiologists label those images accordingly [12]. To automate the mundane conventional task of searching for the best settings for each requirement, our approach looks through sample images and previously designated labels and formulates a relationship between the images and window settings such that each input is catered to the most appropriate window values. A deep learning-based window optimization method is proposed in [13], which involves optimizing the values of the window settings from initial default settings. A cascade approach to improving intracranial hemorrhage detection has also been explored in [14] by using two deep learning models at default and stroke window settings. This approach was successful in improving the sensitivity of hemorrhage detection. Instead of using just one single window settings, a combination can potentially improve the sensitivity of the recognition model. It can be easier to distinguish between lesion and normal regions using a narrower window, especially where it's harder to identify by a broader window alone.

In this invention, window settings are estimated by the network itself without prior information about the default settings. The estimation of the window settings takes place in a distant supervised manner. The deep convolutional network is trained with supervision (since ground truth classification labels are available) but the window settings estimator module is trained without supervision (since the best window settings estimation is not available). While training the deep CNN, the window settings estimator is also simultaneously trained. Once the entire setup has been trained, multiple approximated optimal window settings are selected and combined to improve the overall performance.

SUMMARY

The architecture of our invention consists of three major components. The first component is a window estimation module (a specialized convolutional neural network) and its task is to approximate the appropriate window settings for each input image. The second component is a scaling layer, that uses the window settings approximation and adjusts the brightness and contrast on the input images and converts the input images to grayscale. The third component is a deeper convolutional neural network, with complex architecture designed for accurate multi-class classification. The input to this component is the outputs (grayscale images) from the second component and labels associated with them. This component learns to predict the correct labels from the grayscale images. During this process, any classification error that occurs is propagated back to the first component. Based on the error, the first component updates its approximation scheme to so that it yields better window settings. After iterative training, the first component gets better at approximating the proper window settings for each individual input and the third component gets better at classifying input with least error. While the labels are created by experts looking at a preset window setting for all inputs, our invention looks at each input at the most appropriate window setting (that has been learned) to identify the correct label.

There could be some generalization error, possible during the training of the window estimation module to identify different window settings for each input. Hence, this invention is also used to combine the label predictions based on several window-level (W-L) settings values. Instead of using the W-L setting estimated for each image, a standalone classification network identical to the third component is trained separately with distinct values obtained from statistical analysis of the approximated window settings values. These distinct values include the mean and values that are multiple standard deviations less than the mean. With each of the selected window width and level values, the input images are scaled to corresponding grayscale images. This translates to generating grayscale images at different brightness and contrast from the same input images. Several classification models are trained with these set of grayscales images as input. Our invention combines the predictions from the trained models in two different ways. The first method does an aggregate combination of each of the predictions to result in a final prediction. The second method uses a cascade approach where predictions are re-examined at other models in a sequence with increasing or decreasing window setting.

DETAILED DESCRIPTION

Aspects of the Entire Deep Neural Network Based Architecture

Figure 1:
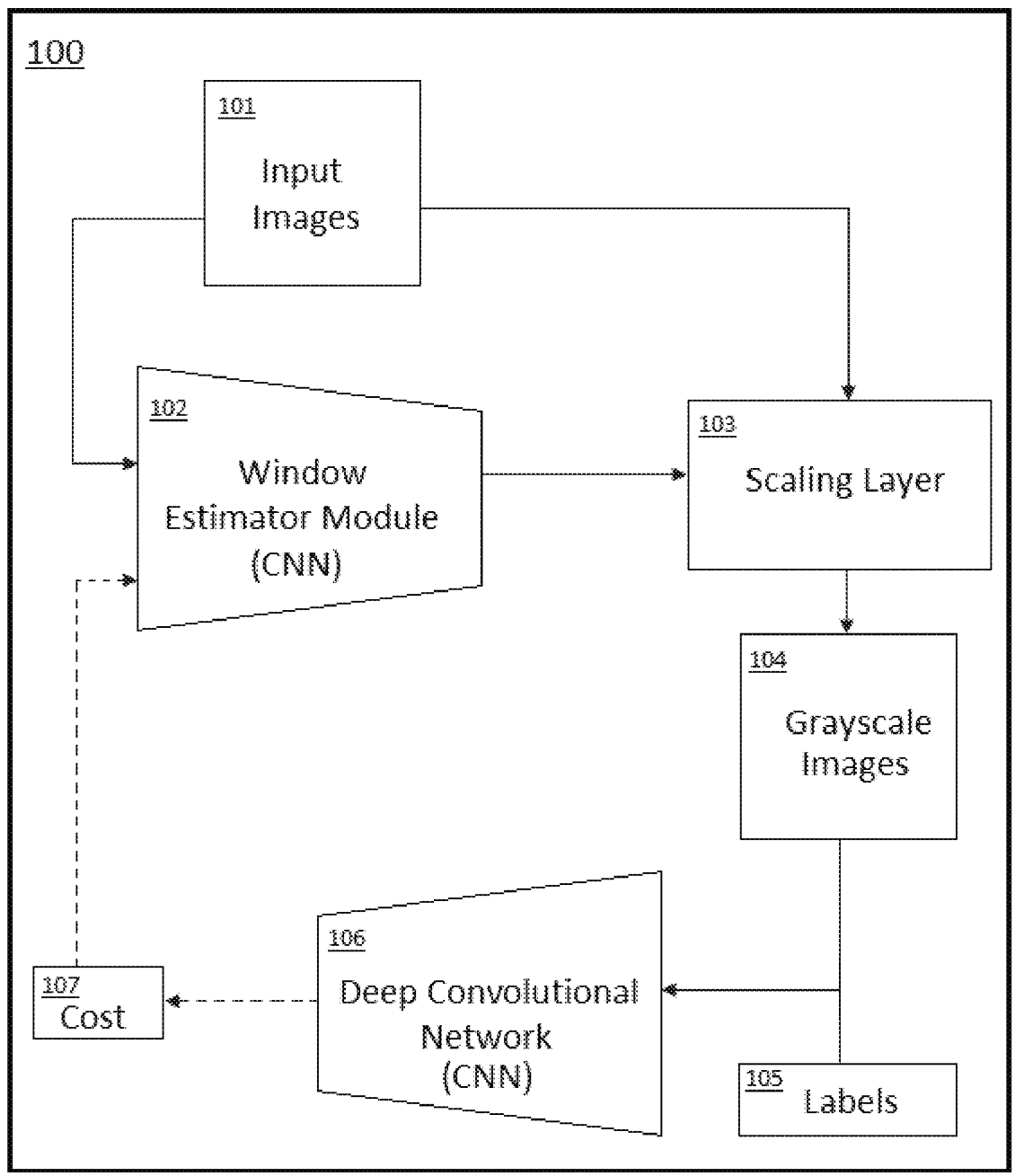
FIG. 1 shows the training workflow of the window estimation, scaling to gray scale and finally segmentation, classification etc. via a deep neural network.

Referring to FIG. 1, a flow chart of the entire process of training the deep learning based architecture that estimates the window-level settings by simultaneously training a deep neural network to classify, segment or predict values based on the given input images 101. The input images are generally in a standard format (for example DICOM) which contains the raw values. With the window settings values estimated by the Window Estimator Module at 102 (a CNN), the scaling layer 103 stretches the contrast of the input and returns a grayscale image. The output grayscale images 104 along with the corresponding labels 105 are sent to a Deep Convolutional Network 106 which can be customized based on the task at hand. Tasks include segmentation of the grayscale image, classifying the image or even predicting a value based on the input. These tasks can be part of medical image diagnostic imaging applications such as disease detection, lesion type classification and segmentation of region of interests. As 106 is learning the task with a supervised learning approach, a cost or loss 107 associated with its performance is calculated. This value is also propagated to the Window Estimator Module 102 so that it improves its estimation of the window settings for best fit as well.

Figure 2:
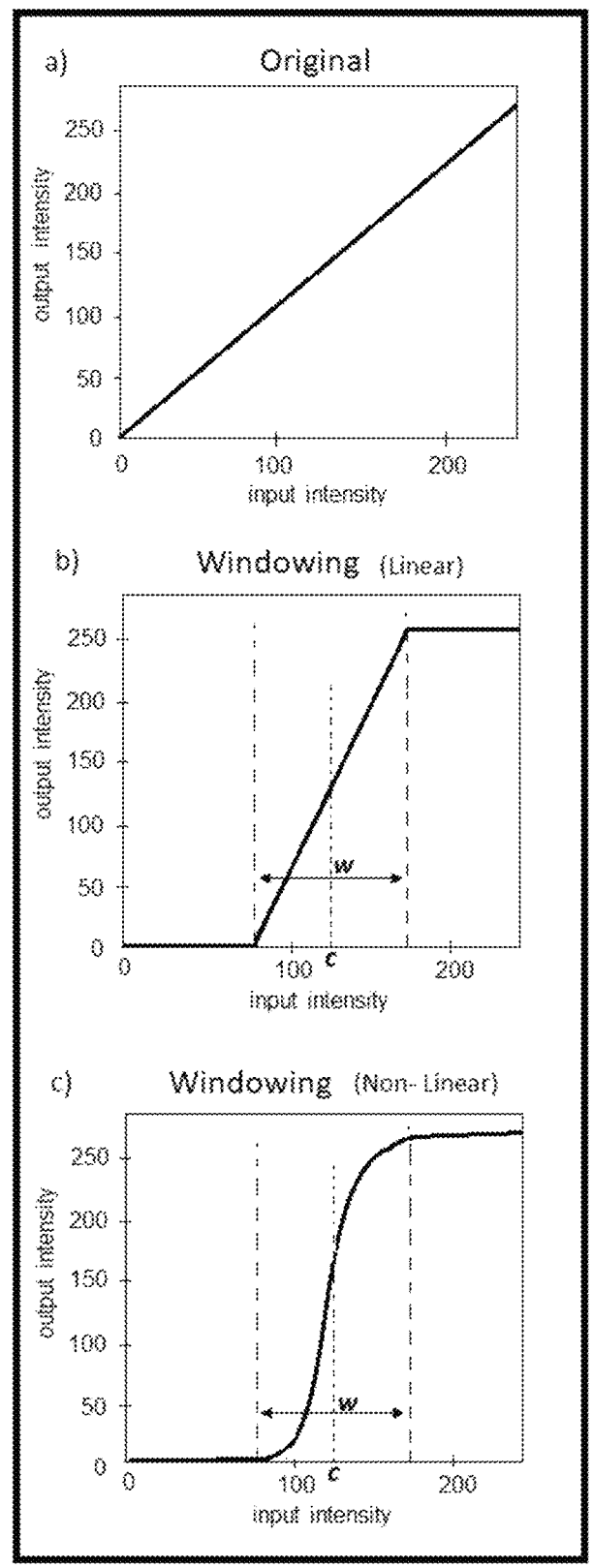
FIG. 2 illustrates different methods of contrast-stretching. The HU (Hounsfield Unit) values common in CT images are chosen for this example, where a) represents the original HU values, b) shows a linear windowing technique and c) shows a non-linear windowing of the original HU values.

FIG. 2 demonstrates the graph of the HU values and the contrast-stretched values. The example on the contrast stretched images show raw intensity values between 80 and 180 stretched to the gray-scale range (0-255). The estimated window values from block 102 is used to scale the input intensity values to the output intensity values. FIG. 2b) shows how the input is contrast stretched with a linear equation whereas FIG. 2c) demonstrates contrast stretching with a non-linear method. In both cases, w and c are the window width and center values respectively.

Figure 3:
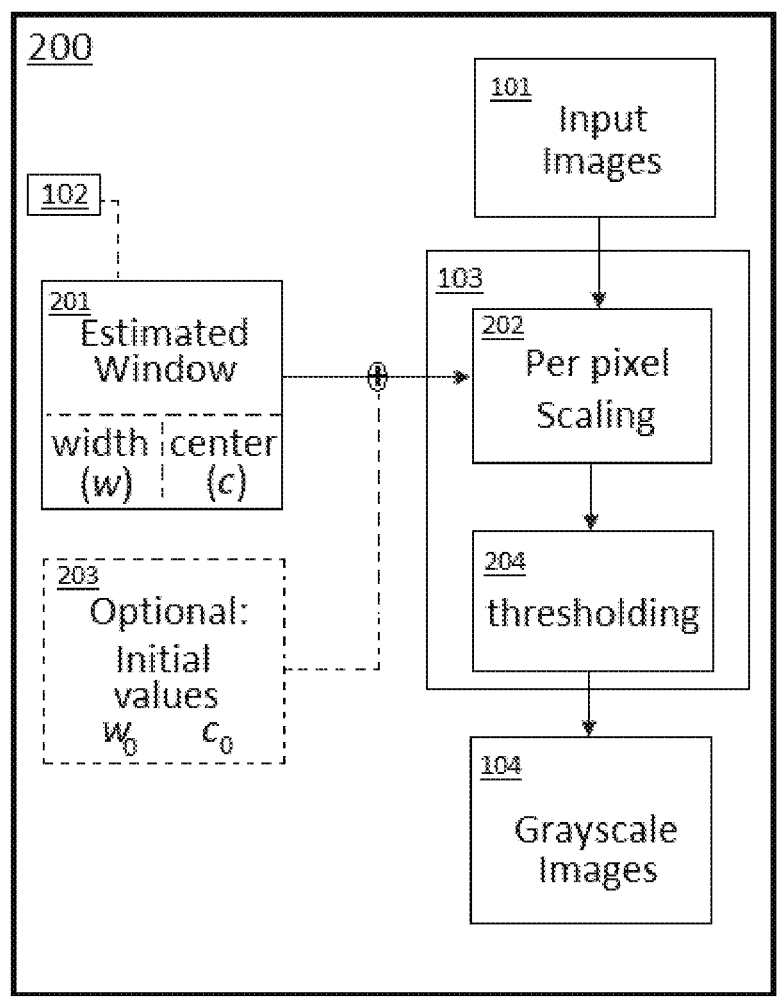
FIG. 3 illustrates the image scaling procedure, for the input with raw values and then thresholding to get grayscale images.

The Scaling Layer 103, for each individual value (pixel) in the input image, converts the HU value to a corresponding grayscale image intensity value (pixel). FIG. 3 demonstrates the how the Scaling Layer component 103 functions. At 202, based on a choice of a linear or non-linear equation, each input value in the input value is rescaled in two steps. At first, the value is transformed with the estimated window 201 from the Window Estimator Module 102. Following that, all values outside the range (0-255) are clipped. Optionally, when default values 203 are known, estimated window values 201 are differences from the default values. The final window width and center presented to the Scaling Layer is the sum of those values from 201 and 203 respectively.

Figure 4:
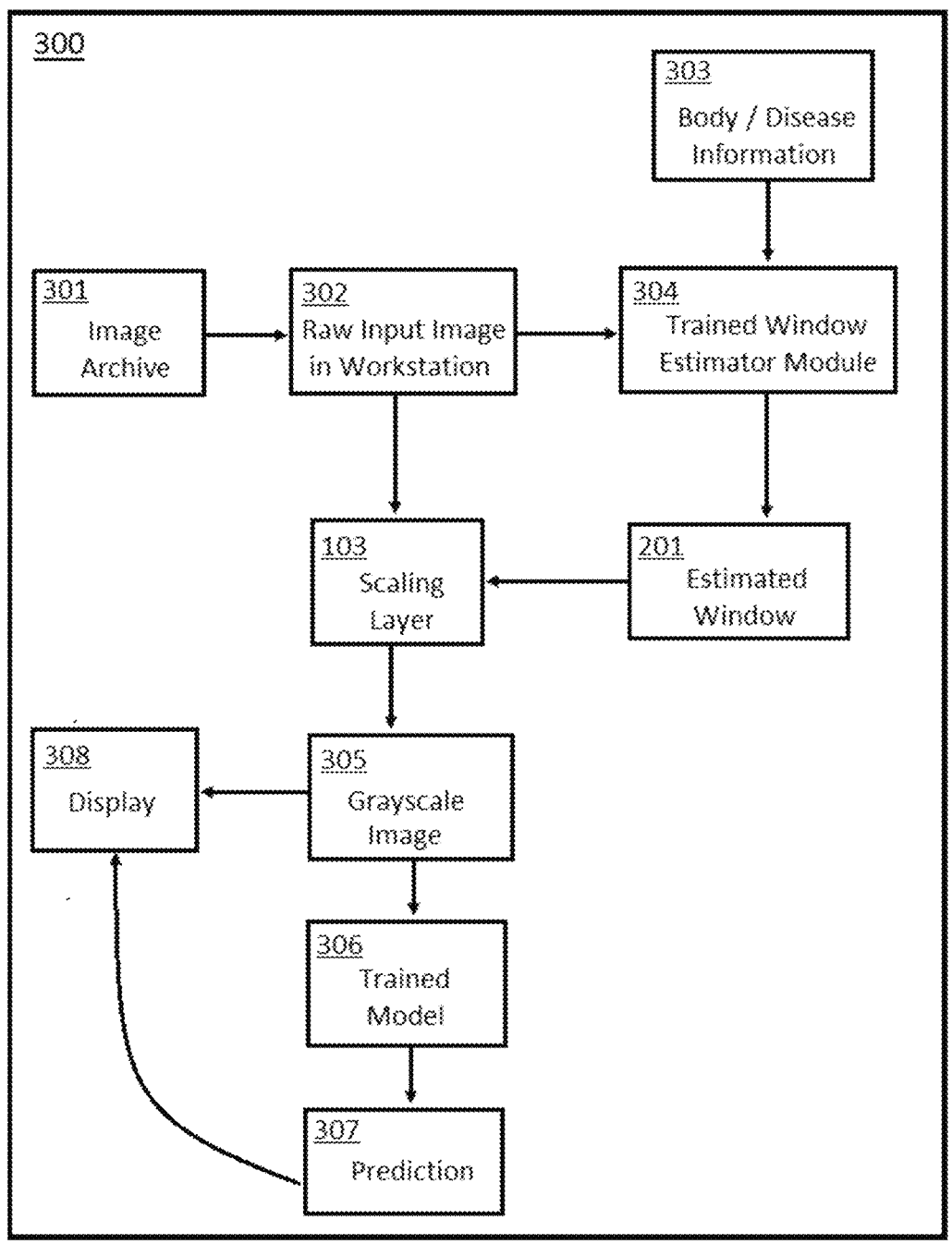
FIG. 4 illustrates the usage of the invention for displaying or for predicting disease/abnormality based on a single raw image.

During the clinical usage as shown in FIG. 4, from the image archive 301, raw input image 302 is retrieved in the workstation. The user selects the body part and/or disease information 303 to choose an appropriate trained window estimator module 304. The scaling layer 103 transforms the raw input image to grayscale 305 at the estimated window. The grayscale image is then shown in the display 308. The grayscale image is then passed through a trained model to predict abnormalities/diseases etc. and the prediction is again shown in the display 308.

Windowing

Figure 5:
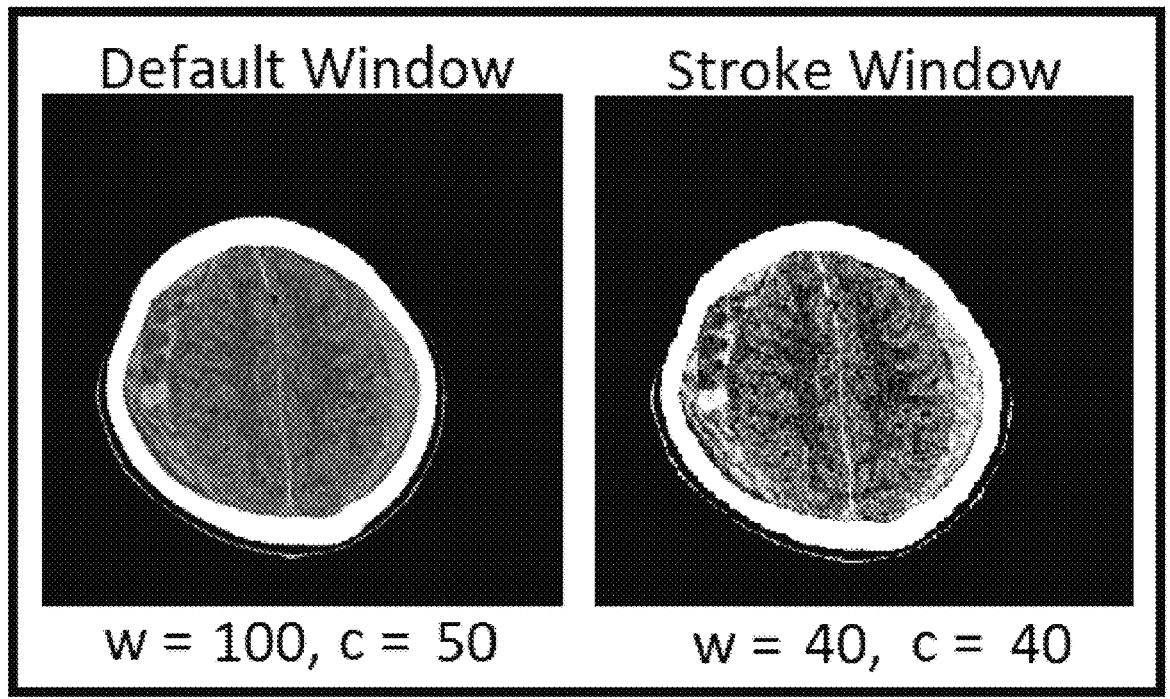
FIG. 5 is an example of two standard window settings for brain CT images where w represents the width and c represents the center of the window.

Different window setting values have been set as default for windowing different anatomies and structures. FIG. 5 is an illustration of two common windows where the first one is the default window settings and the second is at stroke window settings [6]. These are two popular window settings to investigate brain CT images especially for detecting brain strokes. The default window width is 100 and window center is 50 whereas the stroke window width is 40 and window center is also 40. Subtle differences in the default window are highlighted better in the stroke window because increased contrast.

Figure 6:
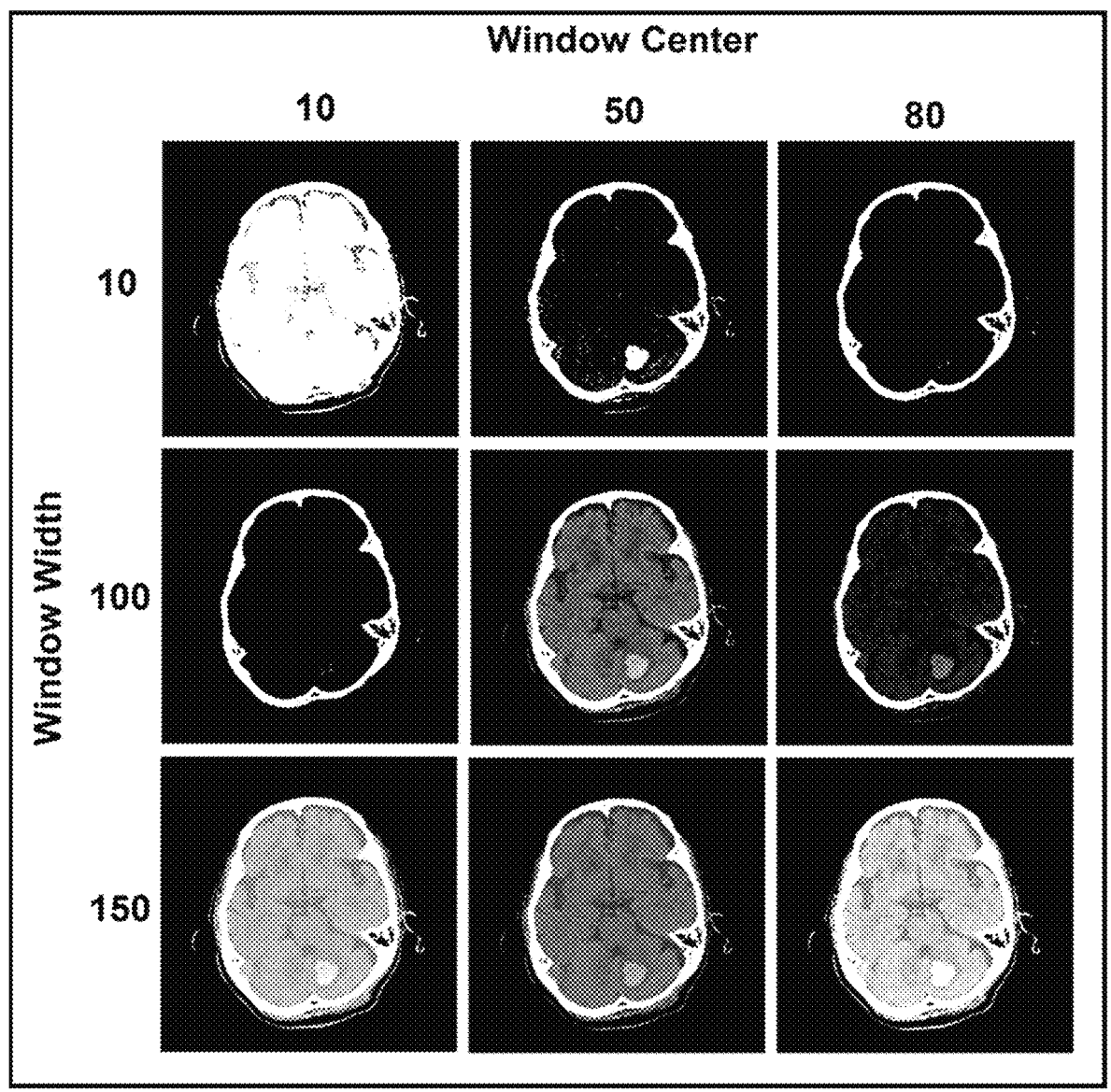
FIG. 6 demonstrates the grayscale image outputs with the changes in window-level settings (width and center) of brain CT images.

Window-Level settings effect the contrast and brightness of the output grayscale images. As the width decreases, the images are closer to binary images. Only values closer and closer to the window center are included and the rest of the values are discarded. FIG. 6 shows examples of brain CTs, only the highly dense bone can be seen in images scaled at the least window width (10) and maximum center (80).

Whereas for the same width and least center (10), all parts of the brain are rescaled to maximum intensity. Increasing the width, as expected, accommodates a lot more values. Hence, the texture on the images can be seen easily and certain regions easily differentiated from the rest. While at a medium window center (50) and minimum window width (10), the lesion and skull are clearly visible, the rest of the brain are not.

Combining Multiple Predictors

Figure 7:
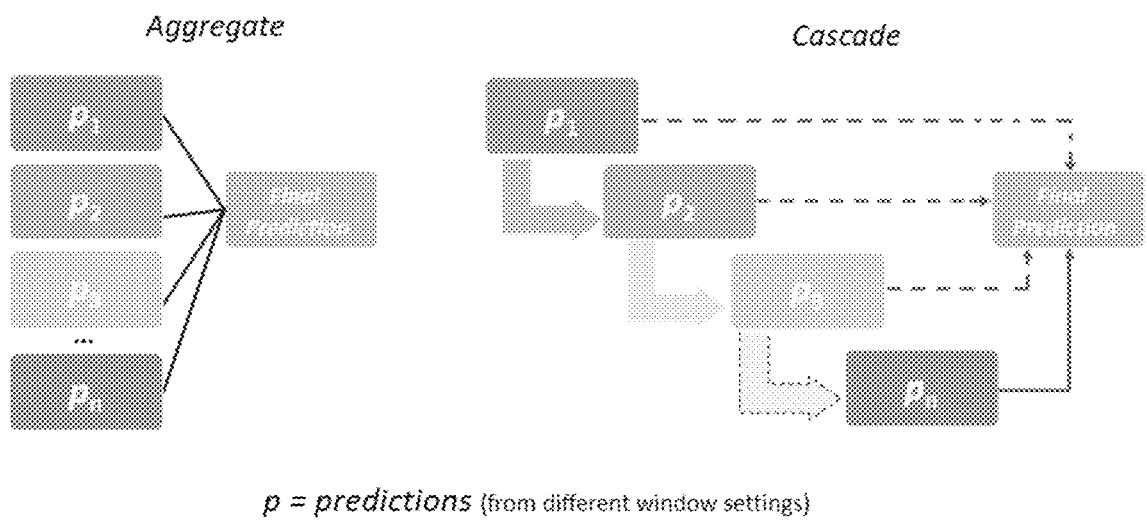
FIG. 7 illustrates how the predictions from multiple window/level settings chosen by statistical analysis of the entirety of predicted window/level settings and combined in aggregate and in cascade approach.

For the purpose of combining the predictions from multiple predictors, the mean and standard deviation of each of the predicted window settings values for all input images are calculated. Following that, one of the two mean values (either width or center) is kept constant, and the other value is decreased or increased to scale the images at a narrower or broader window respectively. The calculated standard deviation acts as the increment/decrement value. This results in several candidate window settings. With each of these window settings pair, the deep classification CNN 106 are trained. This results in an array of predictors that are trained on varying brightness/contrast. After this step, we employ two different methods for combining the predictions of each of these models. FIG. 7, shows the two methods of combining predictions. In both scenarios, the model trained with the mean values of the predicted window settings is assigned as the primary model.

The cascade combination is effective to improve the sensitivity of detecting abnormalities. Each classified input that is deemed to be normal by the primary model, is re-examined at a different window setting. If it is recognized as any 'abnormal' class by a subsequent model, its reclassified as that hemorrhage class. Input images that are classified as being 'normal' by all models at the end of the cascade re-examination retain their 'normal' classification.

For the aggregate combination, every input image is classified by each of the models. The final class for that input is the class identified by the majority of models. If more than half the models do not have the same classification for the input, the classification by primary model is retained.

EXAMPLES

Figure 8:
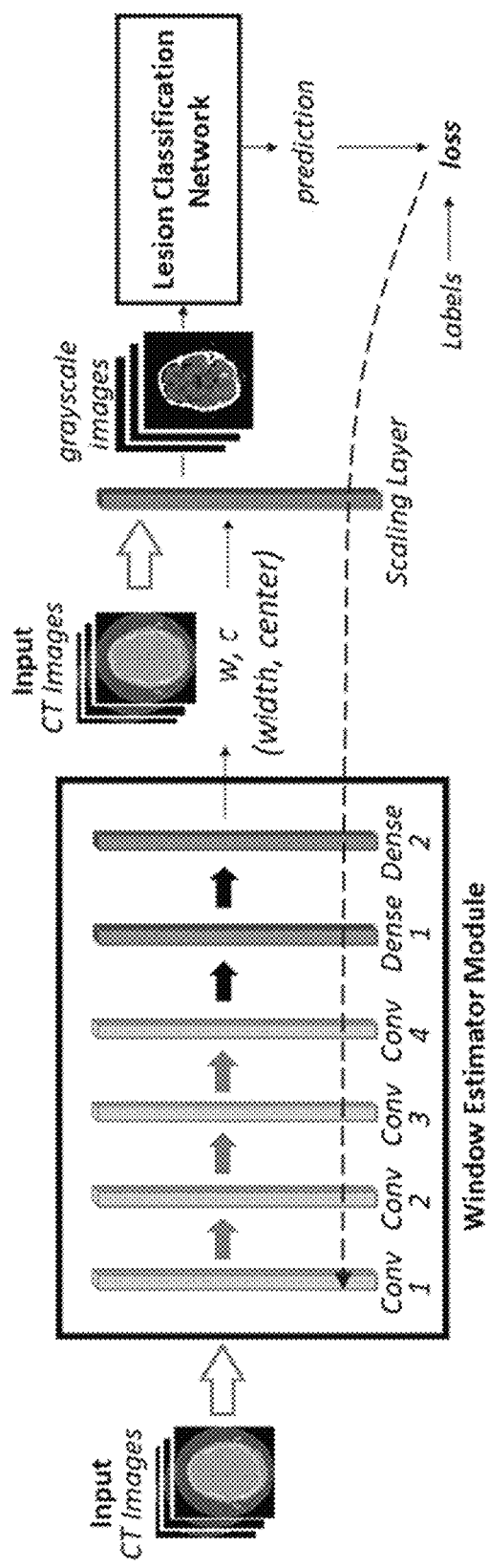
FIG. 8 demonstrates the usage of this invention for hemorrhagic stroke detection from CT images.

FIG. 8 illustrates the usage of our invention for identifying window settings values for detecting the presence of hemorrhagic lesion from Computed Tomography (CT) images. This network also identifies one of six types of intracranial hemorrhage. The window estimator module designed for this detection problem, consists of four layers of convolutional layers followed by two fully connected layers. The final fully connected layer consists of two outputs to produce the window center and window width. Having multiple layers of convolutional layers on the window estimator module can aid in learning the window settings parameters based on both high- and low-level features present in the images. The deep CNN chosen for classification is the Inception-ResNet-v2 architecture [15].

Figure 9:
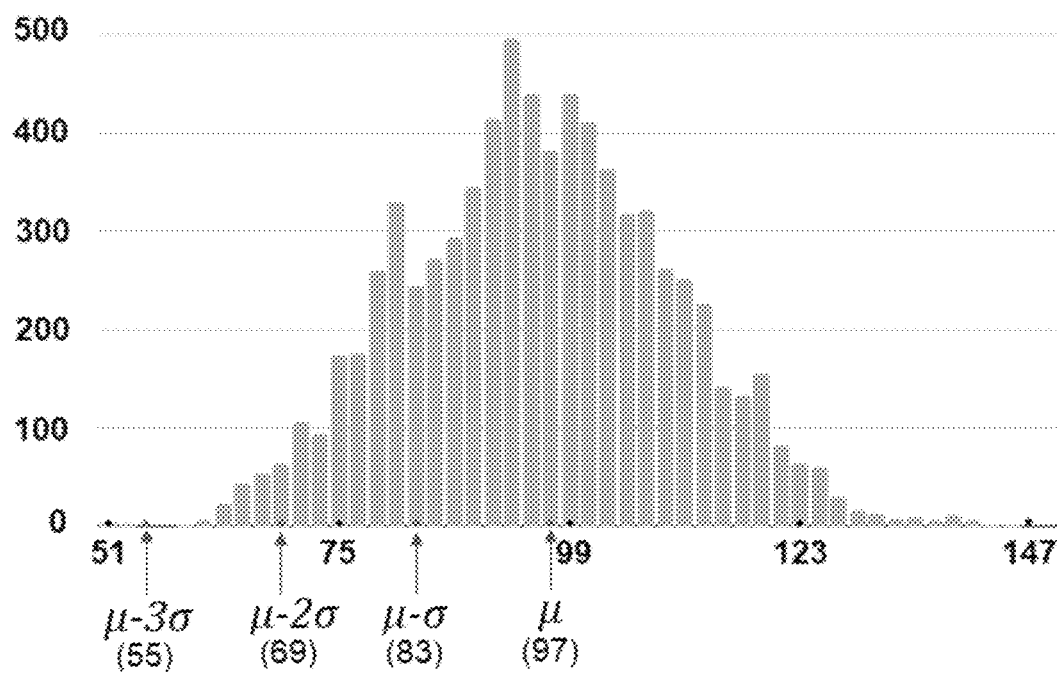
FIG. 9 shows an example of the histogram of predicted window width and window center, where mean center, mean width and widths several standard deviations from mean are highlighted.
Figure 9:
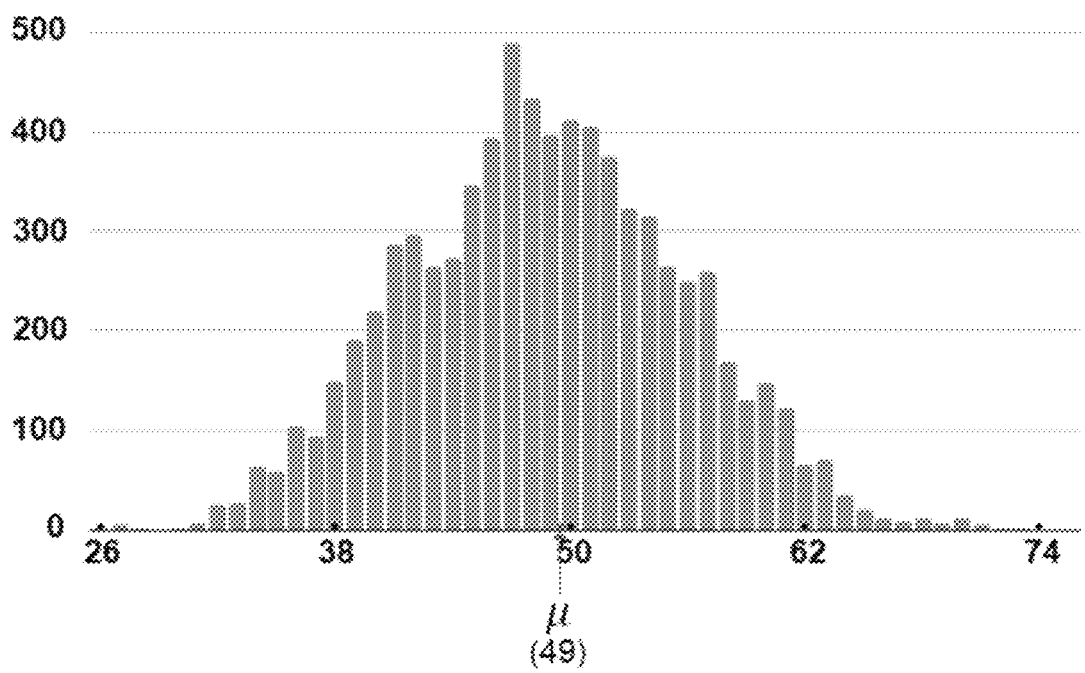

FIG. 9 demonstrates an example of the frequency of window width and window center values estimated for a test dataset of CT images. The chosen window width and window center values are also indicated. In this example, the mean window center is chosen and kept constant and window widths are varied based on mean and standard deviation. This is akin to increasing contrast of the grayscale images.

Figure 10:
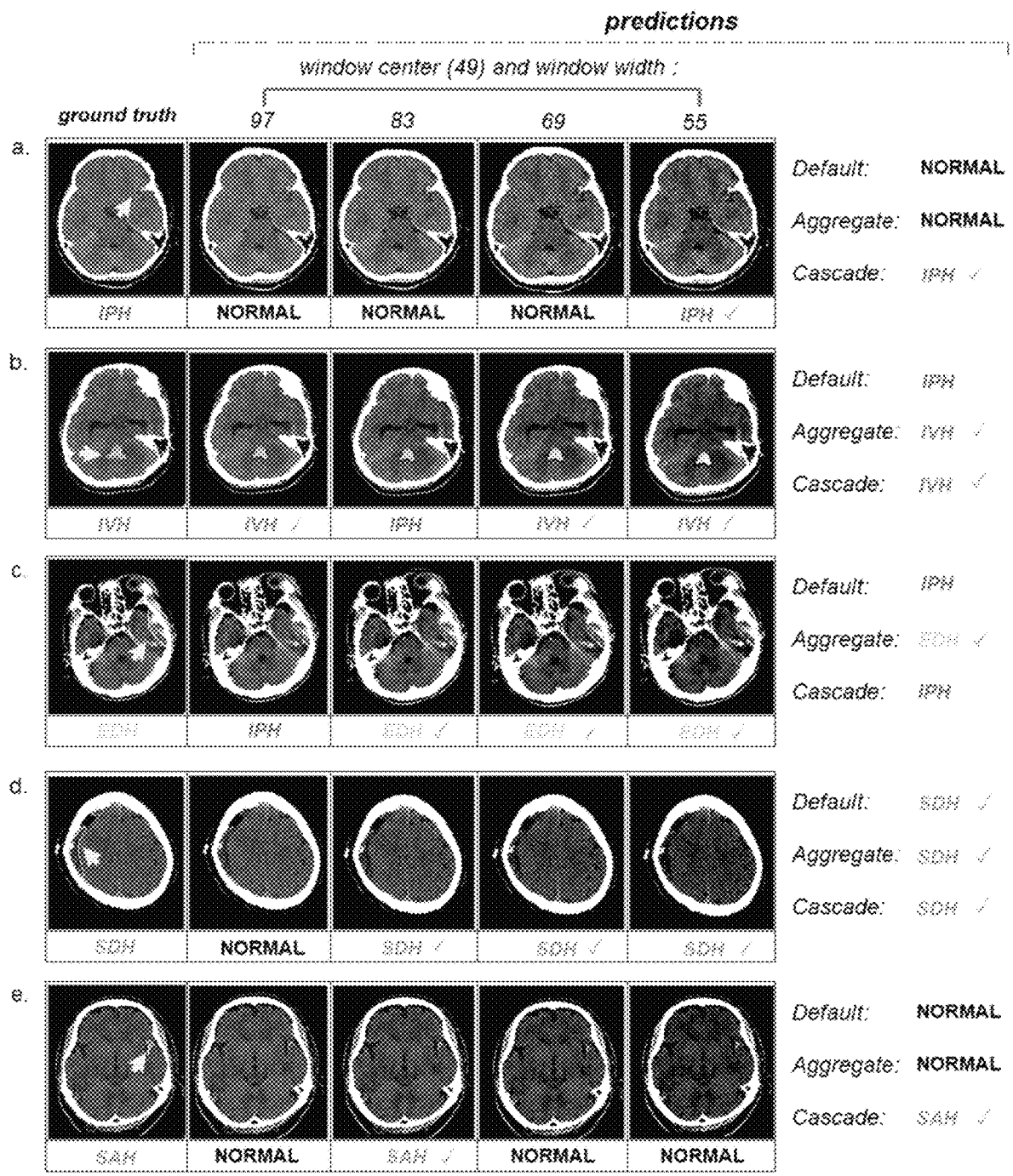
FIG. 10 demonstrates through 5 examples how multiple predictors trained on varying contrast images are combined and yield the final result and compares the result with the default settings approach.

FIG. 10 illustrates 5 examples of ground truth (left most image; shown at default window) and predictions on various windows and combination methods. The ground truth image also contains annotated hemorrhage region. The predicted label is under the images scaled at varying window widths (check mark indicates correct prediction). On the right are the prediction with the default window, as well as the final prediction with aggregate and cascade combinations of the 4 windows on the left.

What is claimed:

1. A method for determining optimum values for brightness and contrast settings by:
   a) estimating initial values for the brightness and contrast settings and modifying raw diagnostic imaging data into grayscale image representation of the diagnostic imaging data;
   b) iteratively updating the estimated the initial values for the brightness and contrast settings, and predicting contents of the raw diagnostic imaging data;
   c) using previously known content of raw diagnostic imaging data, to evaluate the predictions and refine the updates.

2. The method of claim 1 wherein the initial values for the brightness and contrast settings are optionally provided by a user and subsequently updated.

3. The method of claim 1 wherein the optimum values for the brightness and contrast settings are evaluated for each individual data point to modify the raw diagnostic imaging data point into a grayscale image representation.

4. The method of claim 1 wherein each of the most frequently occurring values for the brightness and contrast settings are used to modify the entire raw diagnostic imaging dataset into a corresponding grayscale image dataset.

5. The method of claim 4 wherein each grayscale image dataset is separately parametrized by a computer-implemented training controller along with previously known content of each of the data point in the raw diagnostic imaging dataset.

6. The method for claim 4 wherein each of the parametrized representations of the grayscale images transformed from the raw diagnostic imaging data are combined to improve predictions on unseen raw diagnostic imaging data.

7. The method for claim 6 wherein the final prediction is combinations of predictions made by majority.

8. The method for claim 6 wherein the final prediction is a re-examination of the prediction at a different brightness or contrast.

9. The method of claim 1 wherein the raw diagnostic imaging data is X-ray data.

10. The method of claim 1 wherein the raw diagnostic imaging data is Computed Tomography (CT) data.

11. The method of claim 1 wherein the raw diagnostic imaging data is Magnetic Resonance (MR) data.

* * * * *